United States Patent
Chen et al.

(10) Patent No.: US 12,029,509 B2
(45) Date of Patent: Jul. 9, 2024

(54) ENDODONTIC ROBOTIC SURGICAL SYSTEM AND ENDODONTIC ROBOTIC SURGICAL ASSEMBLY

(71) Applicant: NATIONAL TAIWAN UNIVERSITY, Taipei (TW)

(72) Inventors: Cheng-Wei Chen, Taipei (TW); Yi-Chan Li, Taipei (TW); Hao-Fang Cheng, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 475 days.

(21) Appl. No.: 17/472,714

(22) Filed: Sep. 13, 2021

(65) Prior Publication Data

US 2023/0085313 A1    Mar. 16, 2023

(51) Int. Cl.
*A61B 34/30* (2016.01)
*A61B 90/00* (2016.01)

(52) U.S. Cl.
CPC ............. *A61B 34/30* (2016.02); *A61B 90/06* (2016.02); *A61B 2034/302* (2016.02); *A61B 2090/064* (2016.02)

(58) Field of Classification Search
CPC ....... A61C 1/084; A61C 1/082; A61C 8/0089; A61B 34/30; A61B 90/06; A61B 2090/064; A61B 2017/00323; A61B 1/0051; A61B 1/0057; A61M 25/015; A61M 25/0147

See application file for complete search history.

(56) References Cited

U.S. PATENT DOCUMENTS

| | | | |
|---|---|---|---|
| 6,612,143 B1* | 9/2003 | Butscher | A61C 7/20 72/21.4 |
| 2004/0157188 A1* | 8/2004 | Luth | A61C 1/082 433/75 |
| 2009/0197217 A1* | 8/2009 | Butscher | A61K 31/522 72/6.1 |
| 2019/0247050 A1* | 8/2019 | Goldsmith | A61F 2/82 |
| 2021/0228317 A1* | 7/2021 | Ciriello | A61C 1/082 |
| 2021/0275279 A1* | 9/2021 | Kofford | A61C 8/0001 |
| 2022/0142736 A1* | 5/2022 | Kim | A61C 1/082 |

* cited by examiner

*Primary Examiner* — Cris L. Rodriguez
*Assistant Examiner* — Sydney J Pulvidente

(57) ABSTRACT

An endodontic robotic surgical system is provided. The endodontic robotic surgical system includes a robot arm and an endodontic robotic surgical assembly electrically connected to the robot arm. The endodontic robotic surgical assembly includes a multiple-axis force sensing device, a treatment assembly and an assistive device. The treatment assembly includes a housing, a drawstring-positioning structure disposed on the housing, a plurality of drawstrings connected to the drawstring-positioning structure, and an endodontic surgical element fitted to the housing. The drawstring-positioning structure is electrically connected to the multiple-axis force sensing device. The assistive device is adapted to be put on a tooth structure in a human oral cavity. The drawstrings are connected to different points on the assistive device. An endodontic robotic surgical assembly is further provided.

9 Claims, 4 Drawing Sheets

ENDODONTIC ROBOTIC SURGICAL SYSTEM AND ENDODONTIC ROBOTIC SURGICAL ASSEMBLY

BACKGROUND OF THE INVENTION

1. Field of the Invention

The present disclosure relates to a technique of assisting with endodontic surgery, and in particular to an endodontic robotic surgical system and an endodontic robotic surgical assembly.

2. Description of the Related Art

When carried out by a dentist in one single instance of dental surgery, an endodontic debridement procedure must be performed repeatedly during the surgery, predisposing the dentist to occupational injuries.

When carried out with a robotic system, the endodontic debridement procedure is inevitably confronted with an issue: undesirable movement of the lesion of the patient not anesthetized. Recently, a paper proposed tracking movement of the lesion of a patient not anesthetized, using image aid or optical aid. However, doing so requires an intricate algorithm and thus incurs high cost.

BRIEF SUMMARY OF THE INVENTION

An objective of the present disclosure is to provide an endodontic robotic surgical system and endodontic robotic surgical assembly, so as to automate endodontic debridement procedures, prevent dentists from ending up in occupational injuries, and prevent an automation-induced increase in cost.

The first aspect of the present disclose provides an endodontic robotic surgical system comprising a robot arm and an endodontic robotic surgical assembly. The endodontic robotic surgical assembly comprises a multiple-axis force sensing device, a treatment assembly and an assistive device. The multiple-axis force sensing device is electrically connected to a terminal end of the robot arm. The treatment assembly comprises a housing, a drawstring-positioning structure disposed on the housing, a plurality of drawstrings connected to the drawstring-positioning structure, and an endodontic surgical element fitted to the housing. The drawstring-positioning structure is electrically connected to the multiple-axis force sensing device. The assistive device is adapted to be fitted to a tooth structure in a human oral cavity. The drawstrings are adapted to be connected to different points on the assistive device. The endodontic surgical element is adapted to be controlled by the robot arm to thereby perform endodontic debridement on the tooth structure. The multiple-axis force sensing device is adapted to sense the endodontic surgical element's acting force in the human oral cavity through the drawstring-positioning structure, the drawstrings and the assistive device and send the acting force information to the robot arm, thereby allowing the robot arm to adjust the movement control exercised over the endodontic surgical element.

The second aspect of the present disclose provides an endodontic robotic surgical assembly.

In an embodiment, the treatment assembly further comprises a grip arm and a grip rod, the grip arm extending to the housing and having a fitting hole, and the grip rod being fitted to the fitting hole and having a first end and a second end, the first end being fitted to the housing, and the second end being fitted to the endodontic surgical element.

In an embodiment, the endodontic surgical element is an endodontic file.

In an embodiment, the multiple-axis force sensing device is a six-axis force sensing device.

In an embodiment, the assistive device is a metallic assistive device.

In an embodiment, the drawstring-positioning structure comprises a plurality of protrusions exposed from the housing, wherein the drawstrings are connected to the drawstring-positioning structure from inside and protrude from the drawstring-positioning structure from the protrusions.

In an embodiment, the robot arm comprises a control center for receiving an acting force information of the multiple-axis force sensing device, so as to control the robot arm to move.

Therefore, according to the present disclosure, an endodontic robotic surgical system and an endodontic robotic surgical assembly are conducive to automation of an endodontic debridement procedure and prevention of occupational injuries otherwise caused to dentists. Moreover, the robot arm exercises movement control over an endodontic surgical element in real time with the multiple-axis force sensing function of the endodontic robotic surgical assembly and a drawstring-based displacement estimation technique, thereby dispensing with high-cost image aid or optical aid.

DETAILED DESCRIPTION OF THE INVENTION

To facilitate understanding of the object, characteristics and effects of this present disclosure, embodiments together with the attached drawings for the detailed description of the present disclosure are provided.

Figure 1:
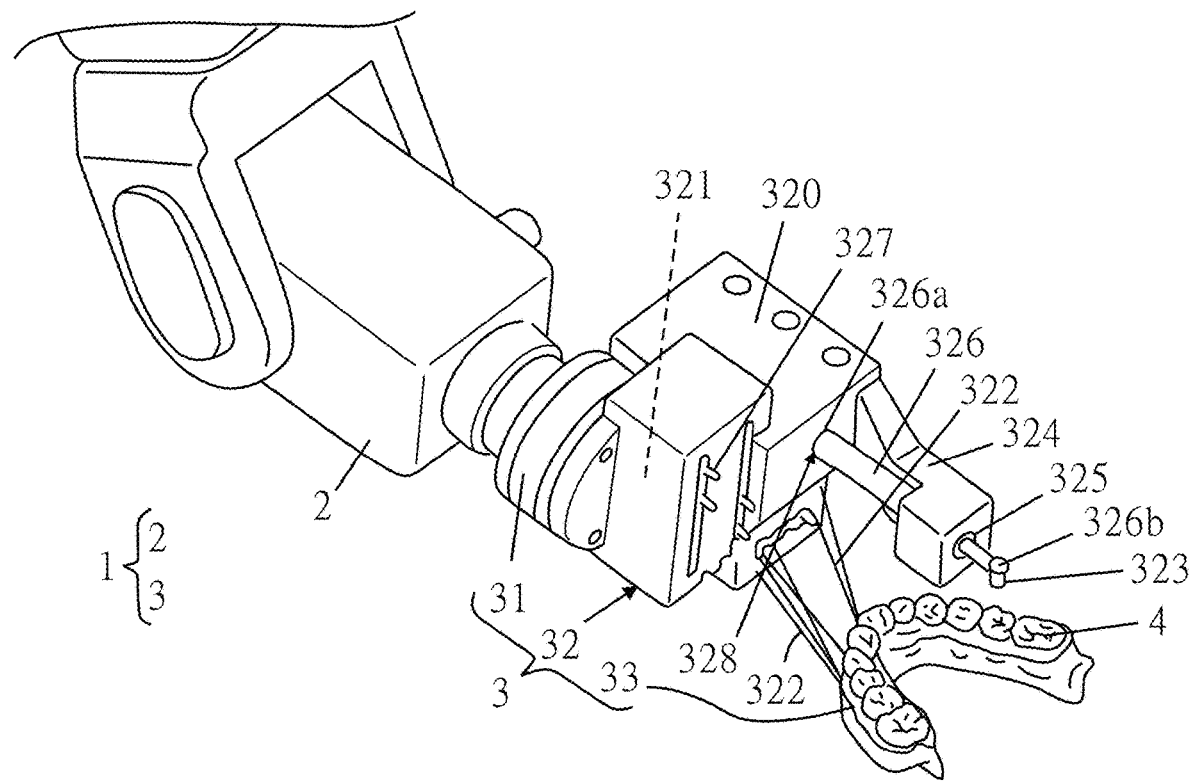
FIG. 1 is a schematic view of an endodontic robotic surgical system applicable to a tooth structure in a human oral cavity according to an embodiment of the present disclosure.
Figure 2:
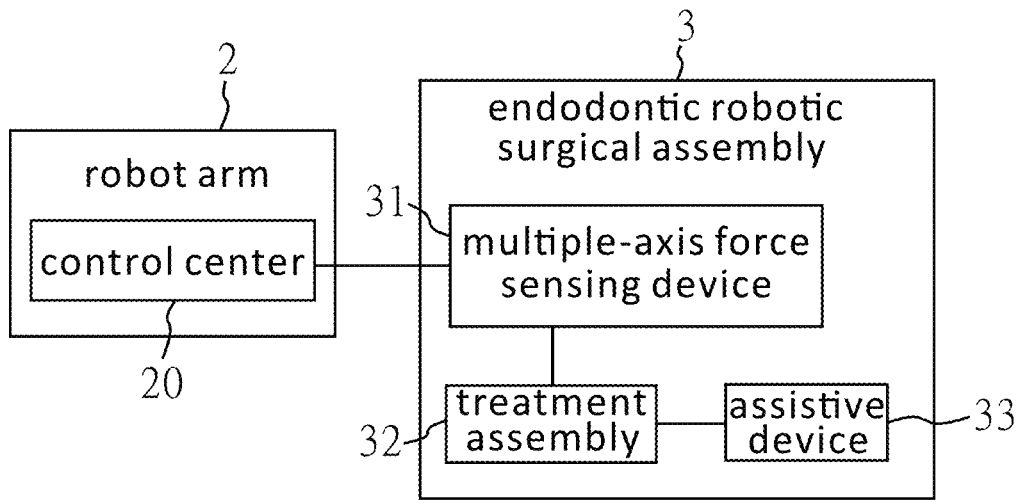
FIG. 2 is a block diagram of the endodontic robotic surgical system according to an embodiment of the present disclosure.
Figure 3:
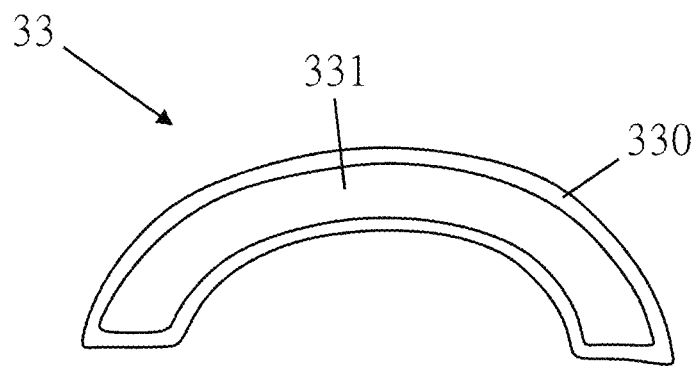
FIG. 3 is a top view an assistive device of an endodontic robotic surgical assembly according to an embodiment of the present disclosure.

Referring to FIG. 1 through FIG. 3, the first aspect of the present disclose provides an endodontic robotic surgical system 1 which comprises a robot arm 2 and an endodontic robotic surgical assembly 3. The endodontic robotic surgical assembly 3 comprises a multiple-axis force sensing device 31, a treatment assembly 32 and an assistive device 33. The multiple-axis force sensing device 31 is electrically connected to a terminal end of the robot arm 2. The treatment assembly 32 comprises a housing 320, a drawstring-positioning structure 321 disposed on the housing 320, a plurality of drawstrings 322 connected to the drawstring-positioning structure 321, and an endodontic surgical element 323 fitted to the housing 320. The housing 320 is connected to the multiple-axis force sensing device 31. The drawstring-positioning structure 321 is electrically connected to the multiple-axis force sensing device 31. The assistive device 33 is adapted to be fitted to a tooth structure 4 in a human oral cavity. The drawstrings 322 are adapted to be connected to different points on the assistive device 33. The endodontic surgical element 323 is adapted to be controlled by the robot arm 2 to thereby perform endodontic debridement on the tooth structure 4. The multiple-axis force sensing device 31 is adapted to sense an acting force between the endodontic surgical element 323 and the tooth structure 4 through the drawstring-positioning structure 321, the drawstrings 322 and the assistive device 33 and send the acting force information to the robot arm 2, thereby allowing the robot arm 2 to adjust the movement control exercised over the endodontic surgical element 323. For example, when the tooth structure 4 stays still, the endodontic surgical element 323 is driven by the robot arm 2 to perform endodontic debridement on the teeth of the tooth structure 4; meanwhile, there is a fixed tension between the tooth structure 4 and the drawstrings 322. However, when the tooth structure 4 moves slightly, the tension between the tooth structure 4 and the drawstrings 322 varies. The multiple-axis force sensing device 31 sends a signal of tension variation to the robot arm 2. Thus, the robot arm 2 adjusts the tilt angle or fine-tuning position of the endodontic surgical element 323, such that the endodontic surgical element 323 can treat the lesion precisely and protect the endodontic surgical element 323 against damage otherwise caused by an inappropriate acting force.

Referring to FIG. 1, the second aspect of the present disclose provides the endodontic robotic surgical assembly 3.

Figure 4:
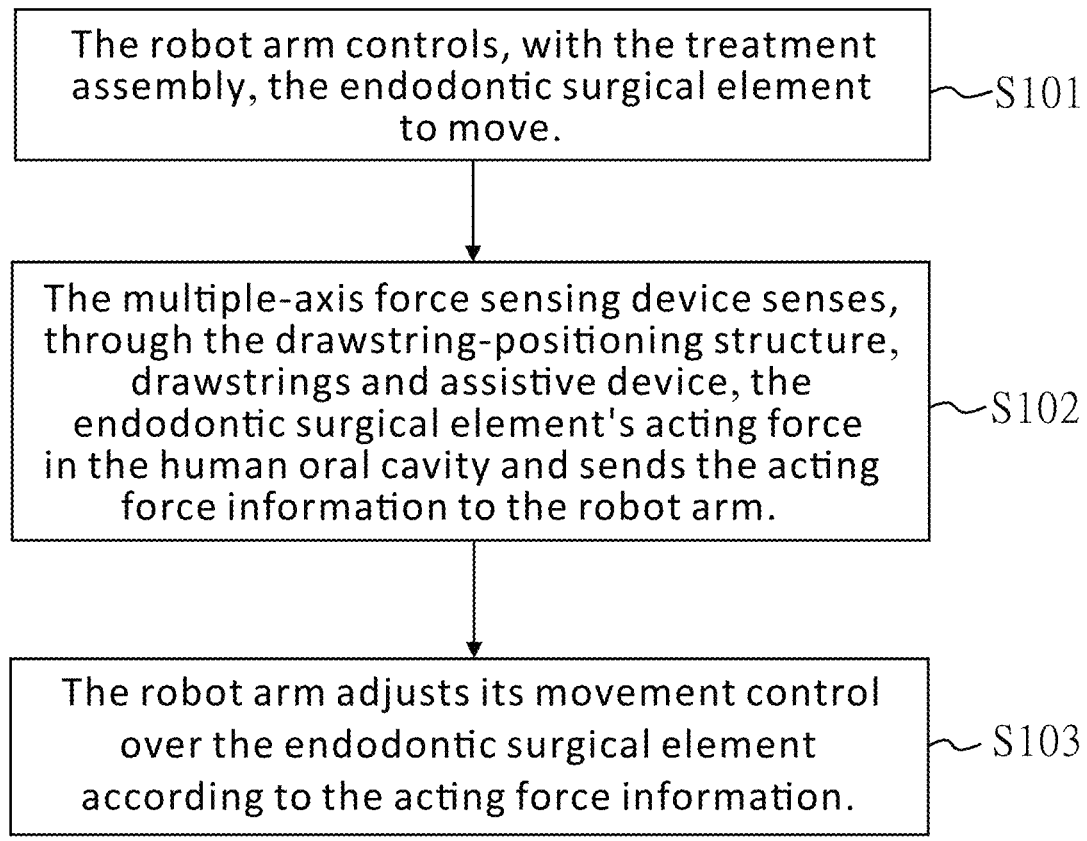
FIG. 4 is a schematic view of the process flow of a method of using the endodontic robotic surgical system according to an embodiment of the present disclosure.

Referring to FIGS. 1 and 4, a method of using the endodontic robotic surgical system 1 comprises the steps below.

Step S101: with the treatment assembly 32, the robot arm 2 controls the endodontic surgical element 323 to move.

Step S102: the multiple-axis force sensing device 31 senses, through the drawstring-positioning structure 321, the drawstrings 322 and the assistive device 33, the acting force between the endodontic surgical element 323 and the tooth structure 4 and sends the acting force information to the robot arm 2.

Step S103: the robot arm 2 adjusts its movement control over the endodontic surgical element 323 according to the acting force information.

Therefore, the endodontic robotic surgical system 1 and endodontic robotic surgical assembly 3 automate endodontic debridement procedures and prevent dentists from ending up in occupational injuries. Furthermore, the robot arm 2 exercises movement control over the endodontic surgical element 323 in real time with the multiple-axis force sensing function of the endodontic robotic surgical assembly 3 and a drawstring-based displacement estimation technique, thereby dispensing with high-cost image aid or optical aid. Furthermore, by fine-tuning the movement of the endodontic surgical element 323 in real time, it is feasible to prevent the endodontic surgical element 323 from severing under an excessive acting force.

Referring to FIG. 1, in an embodiment, the treatment assembly 32 further comprises a grip arm 324 extending to the housing 320. The grip arm 324 has a fitting hole 325. The treatment assembly 32 further comprises a grip rod 326. The grip rod 326 is fitted to the fitting hole 325 and has a first end 326a and a second end 326b. The first end 326a is fitted to the housing 320. The second end 326b is fitted to the endodontic surgical element 323. For instance, the housing 320 has an opening 328 which the first end 326a is inserted into, but the present disclosure is not limited thereto. The endodontic surgical element 323 may also be fitted to the housing 320 by any other means, such as a means of fastening, clamping or latching.

Referring to FIG. 1, in an embodiment, the endodontic surgical element 323 is an endodontic file for performing endodontic debridement on the tooth structure 4, but the present disclosure is not limited thereto. The robot arm 2 is a six-axis robot arm. The multiple-axis force sensing device 31 of the endodontic robotic surgical assembly 3 is electrically connected to the terminal end of the robot arm 2 in the same way as an end effector is.

Referring to FIG. 1, in an embodiment, the multiple-axis force sensing device 31 is a six-axis force sensing device. The drawstrings 322 are connected to the drawstring-positioning structure 321 from inside. The drawstring-positioning structure 321 has a plurality of protrusions 327 exposed from the housing 320 and adapted to enable the drawstrings 322 to protrude from the drawstring-positioning structure 321. The drawstring-positioning structure 321 has therein a plurality of hubs (not shown) which the drawstrings 322 wind around. For instance, by rotating the hubs, it is feasible to adjust the length by which the drawstrings 322 protrude from the drawstring-positioning structure 321 and fix the length by which the drawstrings 322 protrude from the drawstring-positioning structure 321 in order to perform endodontic therapy. With the multiple-axis force sensing device 31 being a six-axis force sensing device, the protrusions 327 are in the number of six, and the drawstrings 322 are in the number of six, but the present disclosure is not limited thereto. The multiple-axis force sensing device 31 is an angle or displacement sensor for converting mechanical motion into electrical signals which can be measured, recorded or transmitted. The drawstrings 322 are metallic wires, for example, stainless steel wires.

Referring to FIG. 1 and FIG. 3, in an embodiment, the assistive device 33 is a metallic assistive device. The assistive device 33 is custom-made to suit the shape of the tooth structure 4 of different patients. The assistive device 33 comprises a frame body 330. The frame body 330 surrounds a fitting slot 331 which the tooth structure 4 is fitted to. The drawstrings 322 are connected to different points on the frame body 330, for example, different points on the outer flange of the frame body 330; thus, the multiple-axis force sensing device 31 precisely senses the tension variations of the drawstrings 322.

Referring to FIG. 1 and FIG. 2, in an embodiment, the robot arm 2 comprises a control center 20. The control center 20 receives the acting force information of the multiple-axis force sensing device 31 in order to control the robot arm 2 to move. The control center 20 is a computer, microcomputer or programmable motherboard. At first, the dentist performs oral cavity tomographic scan on the patient. Then, the region of the tooth structure 4, which endodontic debridement is to be carried out, is defined with the assistive device 33 and according to the result of the tomographic scan; for example, the assistive device 33 exposes the intended endodontic debridement region of the tooth structure 4 according to the result of the tomographic scan. Then, with a human-machine interactive interface, such as a touchscreen, keyboard or mouse, instructions are sent to the control center 20 to control the robot arm 2, thereby controlling the endodontic surgical element 323 to perform endodontic debridement on the tooth structure 4. The control center 20 comes with a built-in algorithm. When the patient moves slightly, the control center 20 senses the movement of the tooth structure 4 through the multiple-axis force sensing device 31 and drawstring-positioning structure 32 and uses the algorithm to figure out the position and posture of the tooth structure 4 to undergo endodontic debridement. Therefore, the patient's fine movement is monitored in real time to reduce surgical risks otherwise caused by the patient's movement.

Figure 5:
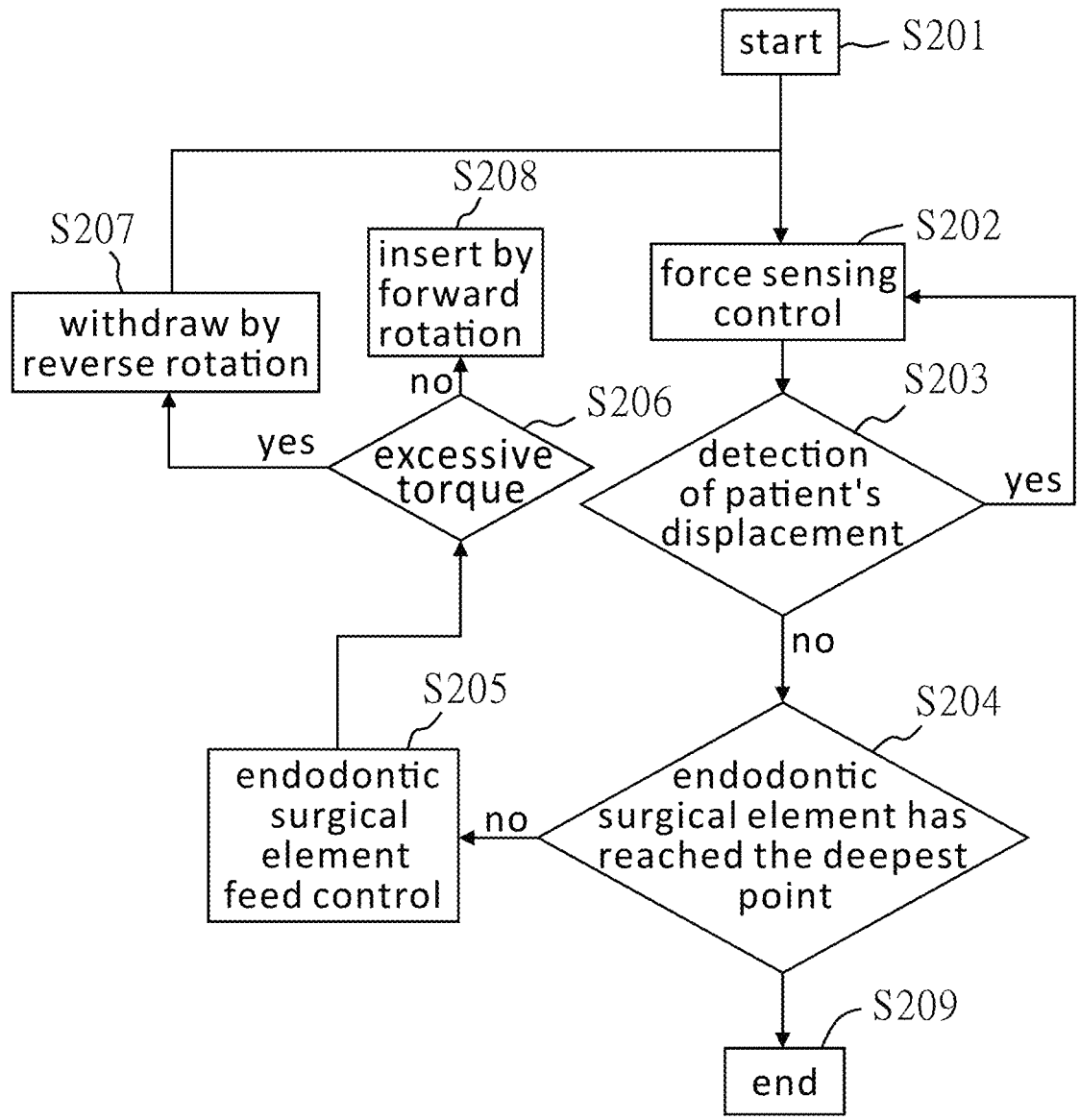
FIG. 5 is a flowchart which details steps S102, S103 of FIG. 4.

Referring to FIG. 5 and FIG. 1, the multiple-axis force sensing device 31 measures the stress exerted on the endodontic surgical element 323 (for example, an endodontic file), whereas the drawstring-positioning structure 321 measures the displacement of the patient's head. The robot arm 2 is moved according to the displacement information provided by the drawstring-positioning structure 321, such that the endodontic surgical element 323 can be aimed at the intended endodontic debridement region of the tooth structure 4. Next, the multiple-axis force sensing device 31 senses the torque exerted on the endodontic file to adjust the posture of the robot arm 2 and the feed rate of the endodontic surgical element 323.

Step S201 is a start step, in which the robot arm 2 starts controlling the endodontic surgical element 323.

Step S202 is about force sensing control, in which the multiple-axis force sensing device 31 starts measuring the stress exerted on the endodontic surgical element 323, and the drawstring-positioning structure 321 starts measuring the displacement of the patient's head. The robot arm 2 adjusts the tilt angle or fine-tuning position of the endodontic surgical element 323 accordingly.

In step S203, upon determination that the patient's displacement is sensed persistently, the process flow goes to step S202, otherwise goes to step S204. Step S203 further involves determining whether the endodontic surgical element 323 has reached the deepest point, and the process flow goes to step S209 upon an affirmative determination, ending the endodontic debridement procedure.

In step S204, upon detection that the endodontic surgical element 323 has not reached the deepest point, it indicates that the endodontic debridement procedure has not finished, and thus the process flow goes to step S205, thereby adjusting the feed rate of the endodontic surgical element 323.

In step S206, upon detection of an excessive torque of the endodontic surgical element 323, the process flow goes to step S207 to withdraw the endodontic surgical element 323 by rotating it reversely before going back to step S202. If no excessive torque of the endodontic surgical element 323 is detected, the process flow will go to step S208 to insert the endodontic surgical element 323 by forward rotation thereof before going back to step S202. The endodontic therapy is fully carried out with one or more procedures.

While the present disclosure has been described by means of specific embodiments, numerous modifications and variations could be made thereto by those skilled in the art without departing from the scope and spirit of the present disclosure set forth in the claims.

What is claimed is:

1. An endodontic robotic surgical system, comprising:
a robot arm; and
an endodontic robotic surgical assembly comprising a multiple-axis force sensing device, a treatment assembly and an assistive device;
wherein the multiple-axis force sensing device is electrically connected to a terminal end of the robot arm;
wherein the treatment assembly comprises a housing, a drawstring-positioning structure disposed on the housing, a plurality of drawstrings connected to the drawstring-positioning structure, and an endodontic surgical element fitted to the housing, with the drawstring-positioning structure being electrically connected to the multiple-axis force sensing device;
wherein the assistive device is adapted to be fitted to a tooth structure in a human oral cavity, and the drawstrings are adapted to be connected to different points on the assistive device;
wherein the endodontic surgical element is adapted to be controlled by the robot arm to thereby perform endodontic debridement on the tooth structure, whereas the multiple-axis force sensing device is adapted to sense the endodontic surgical element's acting force in the human oral cavity with the drawstring-positioning structure, the drawstrings and the assistive device and sends an acting force information to the robot arm, thereby allowing the robot arm to adjust movement control exercised over the endodontic surgical element.

2. The endodontic robotic surgical system of claim 1, wherein the treatment assembly further comprises a grip arm and a grip rod, the grip arm extending to the housing and having a fitting hole, and the grip rod being fitted to the fitting hole and having a first end and a second end, the first end being fitted to the housing, and the second end being fitted to the endodontic surgical element.

3. The endodontic robotic surgical system of claim 1, wherein the endodontic surgical element is an endodontic file.

4. The endodontic robotic surgical system of claim 1, wherein the multiple-axis force sensing device is a six-axis force sensing device.

5. The endodontic robotic surgical system of claim 1, wherein the assistive device is a metallic assistive device.

6. The endodontic robotic surgical system of claim 1, wherein the drawstring-positioning structure comprises a plurality of protrusions exposed from the housing, wherein the drawstrings are connected to the drawstring-positioning structure from inside and protrude from the drawstring-positioning structure from the protrusions.

7. The endodontic robotic surgical system of claim 1, wherein the robot arm comprises a control center for receiving an acting force information of the multiple-axis force sensing device, so as to control the robot arm to move.

8. An endodontic robotic surgical assembly, applicable to a robot arm, the endodontic robotic surgical assembly comprising:
a multiple-axis force sensing device electrically connected to a terminal end of the robot arm;
a treatment assembly comprising a housing, a drawstring-positioning structure disposed on the housing, a plurality of drawstrings connected to the drawstring-positioning structure, and an endodontic surgical element fitted to the housing, wherein the drawstring-positioning structure is electrically connected to the multiple-axis force sensing device; and
an assistive device adapted to be fitted to a tooth structure in a human oral cavity, wherein the drawstrings are adapted to be connected to different points on the assistive device;
wherein the endodontic surgical element is adapted to be controlled by the robot arm to thereby perform endodontic debridement on the tooth structure, whereas the multiple-axis force sensing device is adapted to sense the endodontic surgical element's acting force in the human oral cavity with the drawstring-positioning structure, the drawstrings and the assistive device and send an acting force information to the robot arm, thereby allowing the robot arm to adjust control exercised over the endodontic surgical element.

9. The endodontic robotic surgical assembly of claim 8, wherein the housing extends to form a grip arm with a fitting hole, whereas the treatment assembly further comprises a grip rod, the grip rod being fitted to the fitting hole and having a first end and a second end, the first end being fitted to the housing, and the second end being fitted to the endodontic surgical element.

* * * * *